US006865753B2

(12) United States Patent
Nishida

(10) Patent No.: US 6,865,753 B2
(45) Date of Patent: Mar. 15, 2005

(54) GOGGLES

(75) Inventor: Keiko Nishida, Izumi (JP)

(73) Assignee: Yamamoto Kogaku Co., Ltd., Osaka (JP)

( * ) Notice: Subject to any disclaimer, the term of this patent is extended or adjusted under 35 U.S.C. 154(b) by 0 days.

(21) Appl. No.: 10/229,579

(22) Filed: Aug. 28, 2002

(65) Prior Publication Data

US 2003/0093854 A1 May 22, 2003

(30) Foreign Application Priority Data

Aug. 28, 2001  (JP) ........................................ 2001-258621

(51) Int. Cl.$^7$ ................................................ A61F 9/02
(52) U.S. Cl. .............................................. 2/426; 2/452
(58) Field of Search ............................ 2/426, 428, 438, 2/439, 440, 442, 12, 13, 15, 452; 24/615, 625

(56) References Cited

U.S. PATENT DOCUMENTS

| | | | | | |
|---|---|---|---|---|---|
| 4,150,464 A | * | 4/1979 | Tracy | ........................... | 24/313 |
| 4,825,515 A | * | 5/1989 | Wolterstorff, Jr. | ............ | 24/625 |
| 5,084,946 A | * | 2/1992 | Lee | ............................. | 24/625 |
| 5,584,105 A | * | 12/1996 | Krauss | ........................ | 24/614 |
| 5,657,493 A | * | 8/1997 | Ferrero et al. | .................. | 2/428 |
| 5,774,956 A | * | 7/1998 | French et al. | .................. | 24/625 |
| 5,926,928 A | * | 7/1999 | Lundstedt | ..................... | 24/625 |
| 6,163,942 A | * | 12/2000 | Liao | ............................. | 24/625 |
| 6,263,549 B1 | * | 7/2001 | Uehara | ........................ | 24/625 |
| 6,405,384 B1 | * | 6/2002 | Chiang | ......................... | 2/428 |
| 6,421,889 B1 | * | 7/2002 | Chien | .......................... | 24/614 |
| 6,446,272 B1 | * | 9/2002 | Lee | .............................. | 2/428 |
| 6,460,232 B2 | * | 10/2002 | Maruoka | ..................... | 24/615 |
| 6,507,982 B2 | * | 1/2003 | Kawamura | ................... | 24/615 |

* cited by examiner

Primary Examiner—Gary L. Welch
(74) Attorney, Agent, or Firm—Koda & Androlia

(57) ABSTRACT

Goggles have a goggle body and a headband which are attached together on both of respective end portions thereof through respective connecting members. Each end portion of the goggle body has fitting apertures open upwardly and downwardly, and an insertion path connecting to the fitting apertures and open to a lateral end side. Furthermore each connecting member has resilient insertion pieces with protruded portions, and the protruded portions fit in the fitting apertures and come out upwardly and downwardly. At the time of detaching the connecting member from the goggle body, a wearer can easily and reliably manipulate the connecting means with his or her thumb and index finger, not only his or her thumb. And a reliable connection between the goggle body and the connecting member is obtained, and, even an outer force coming from front does not cause an inadvertent separation of them in use.

6 Claims, 9 Drawing Sheets

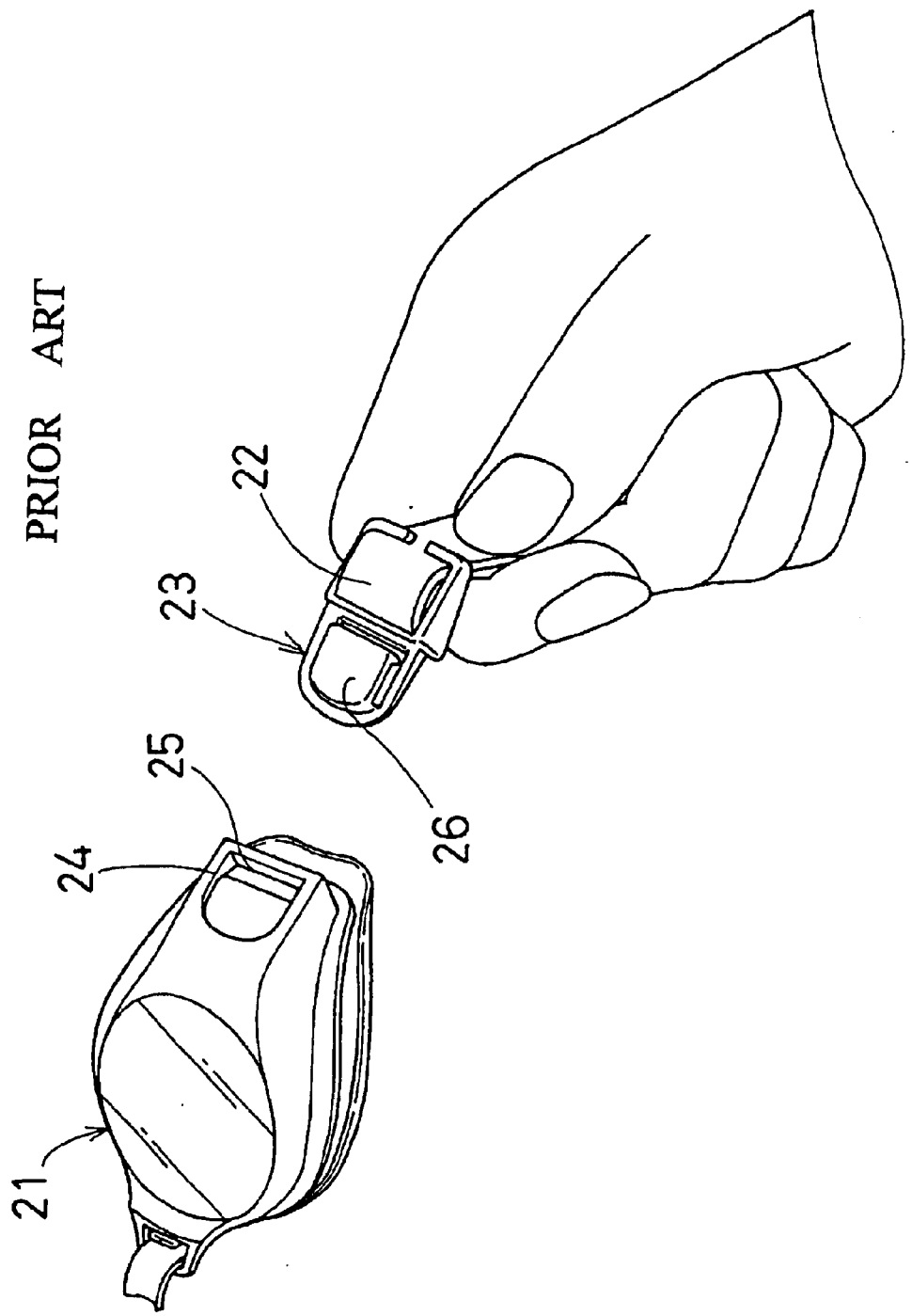

GOGGLES

TECHNICAL FIELD OF THE INVENTION

The present invention relates to goggles, more particularly goggles used in swimming, skiing, other various kinds of sports or the like.

DESCRIPTION OF THE RELATED PRIOR ART

Conventional goggles of this type, for example, as shown in FIG. 9, have a goggle body 21 and a headband 22. Both ends of the headband 22 are connected with both ends of the goggle body 21 through respective connecting members 23 (the drawings show only one end). One end portion of the goggle body 21 has a fitting aperture 24 and an insertion hole 25. The fitting aperture 24 is open to a front side and the insertion hole 25 connects to the fitting aperture 24 and is open to a lateral end side. The connecting member 23 has, on its end portion, a resilient piece 26 to project out to the front side.

At the time of connecting the goggle body 21 and the connecting member 23, a user holds the connecting member 23 with his or her thumb and index finger to press the resilient piece 26 down, and inserts the pressed resilient piece 26 into the insertion hole 25 of the goggle body 21 to let it fit and settle in the fitting aperture 24.

On the other hand, at the time of releasing the connecting member 23 from the goggle body 21, he or she presses down the resilient piece 26 settled in and exposed from the fitting aperture 26 with his or her thumb and pulls the connecting member 23 out in a separation direction.

In the above prior art goggles, however, it is not easy for a user to press down the resilient piece 26 with his or her thumb and pull it out in the separation direction at the time of releasing the connecting member 23 from the goggle body 21, and he or she cannot do so without fail. And it is a problem that the goggle body 21 and the connecting member 23 are not readily released from each other.

In the above prior art goggles, at the time of connecting the goggle body 21 and the connecting member 23, even if a user thinks he or she has inserted the resilient piece 26 properly in the fitting aperture, the case that the resilient piece 26 is actually not fitted in the fitting aperture properly sometimes happens. The use of goggles in this state may result in the problem that the goggle body 21 and the connecting member 23 inadvertently separate from each other in use.

Furthermore, in the above prior art goggles, during the use of the goggles after connecting the goggle body 21 and the connecting member 23 together, because being at the front side, the resilient piece 26 is liable to directly receive an outer force such as a hitting force of a foreign matter thereagainst. This may cause the resilient piece 26 to be pressed down and come off from the fitting aperture 24, and finally results in separation between the goggle body 21 and the connecting member 23. This is another problem.

SUMMARY OF THE INVENTION

The present invention, therefore, is made to resolve the above mentioned problems. It is an object of the present invention to provide goggles which enables a user to reliably and easily separate a connecting member from a goggle body with his or her thumb and index finger, not only his or her thumb, at the time of separation thereof, and to connect the goggle body and the connecting member in a secured fashion, and in which the connection of the goggle body and the connecting member is not released in use even if an outer force from front is applied.

In order to achieve the above object, goggles according to the present invention includes a goggle body and a headband, both end portions of the goggle body are connected with both end portions of the headband through respective connecting members. Each of the end portions of the goggle body has fitting apertures open upward and downward and an insertion path having an insertion port which connects to the fitting apertures and opens to a lateral end side. Furthermore, each of the connecting members has, on its end portion, resilient insertion pieces with protruded portions which project out upwardly and downwardly when settled in the fitting apertures.

The goggles according to the present invention may have the fitting apertures in recessed portions formed at the end portions of the goggles.

In the goggles according to the present invention, the insertion path may be provided with a guide groove formed in an insertion direction of the connecting member, and the connecting member may be provided with a guide piece between the resilient insertion pieces at the end portion. The guide piece has a rib which is received in and guided along with the guide groove.

The above and other objects, features and advantages of the present invention will become apparent from the following description in conjunction with the accompanying drawings.

BRIEF DESCRIPTION OF THE DRAWINGS

FIG. 9 is a perspective view showing a state in which a goggle body and a connecting member of prior art goggles are separated from each other.

DETAILED DESCRIPTION OF THE INVENTION

Figure 1:
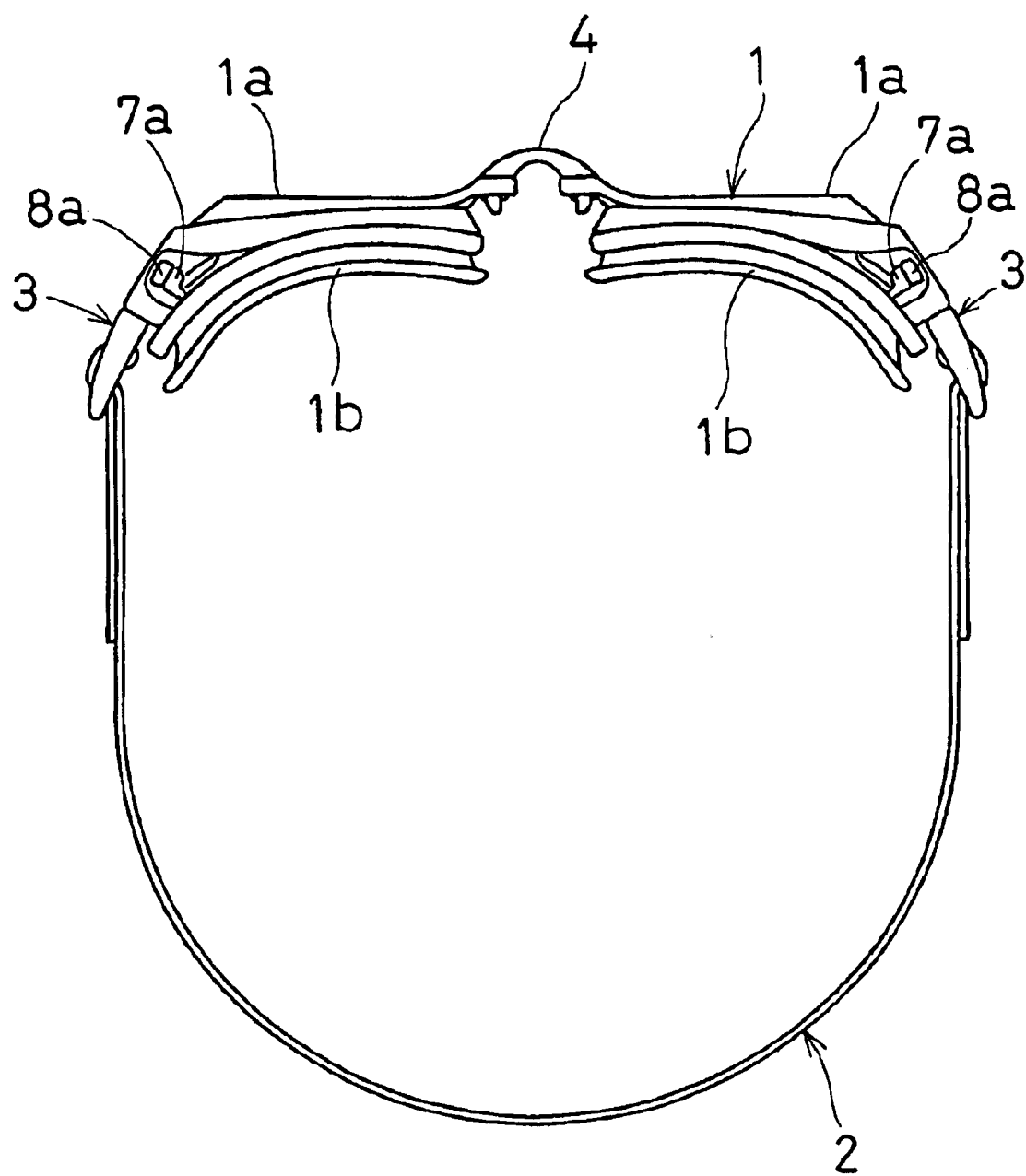
FIG. 1 is a plan view showing an embodiment of goggles according to the present invention.
Figure 2:
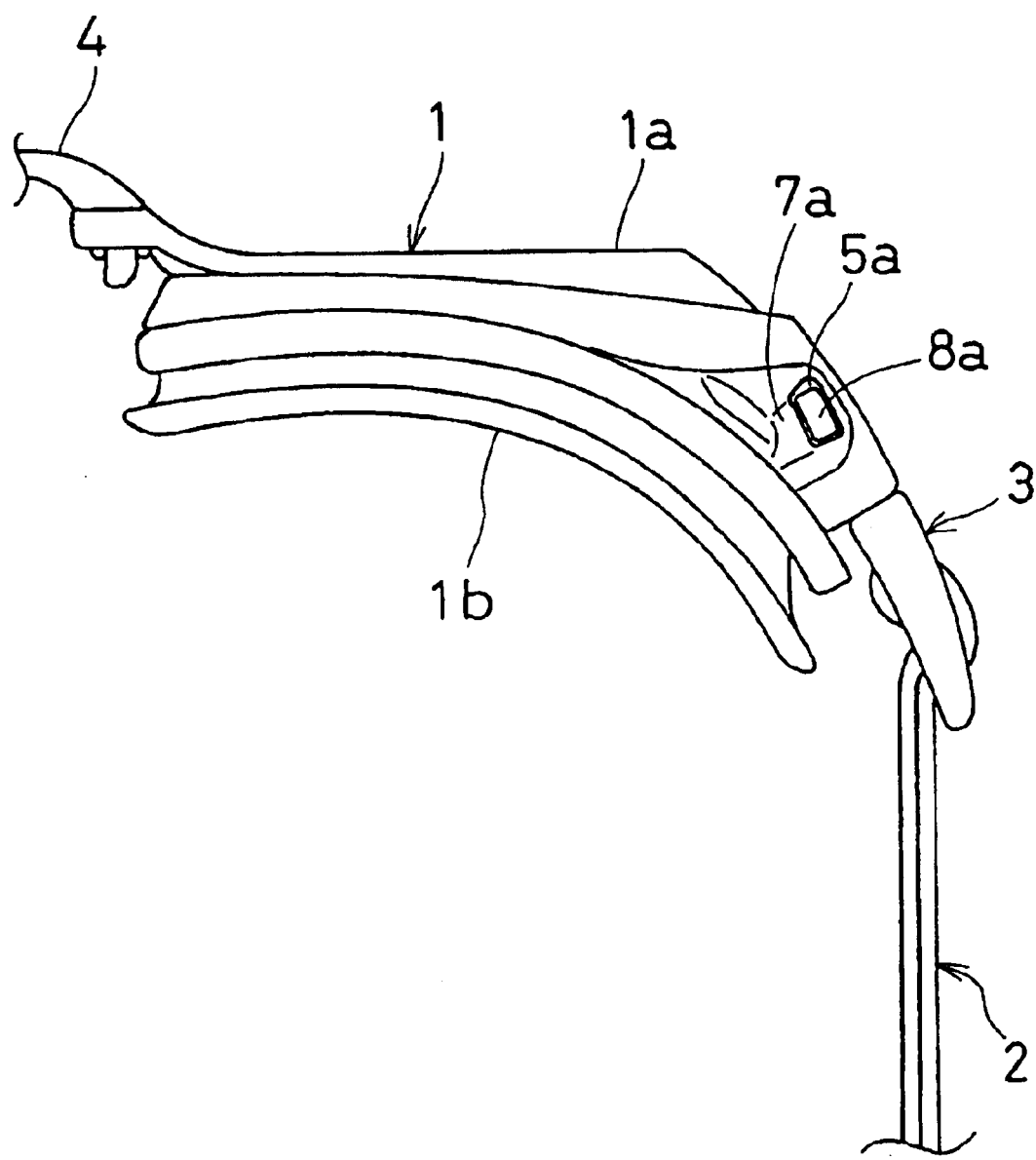
FIG. 2 is an enlarged plan view showing essential parts of the goggles according to the present invention.
Figure 3:
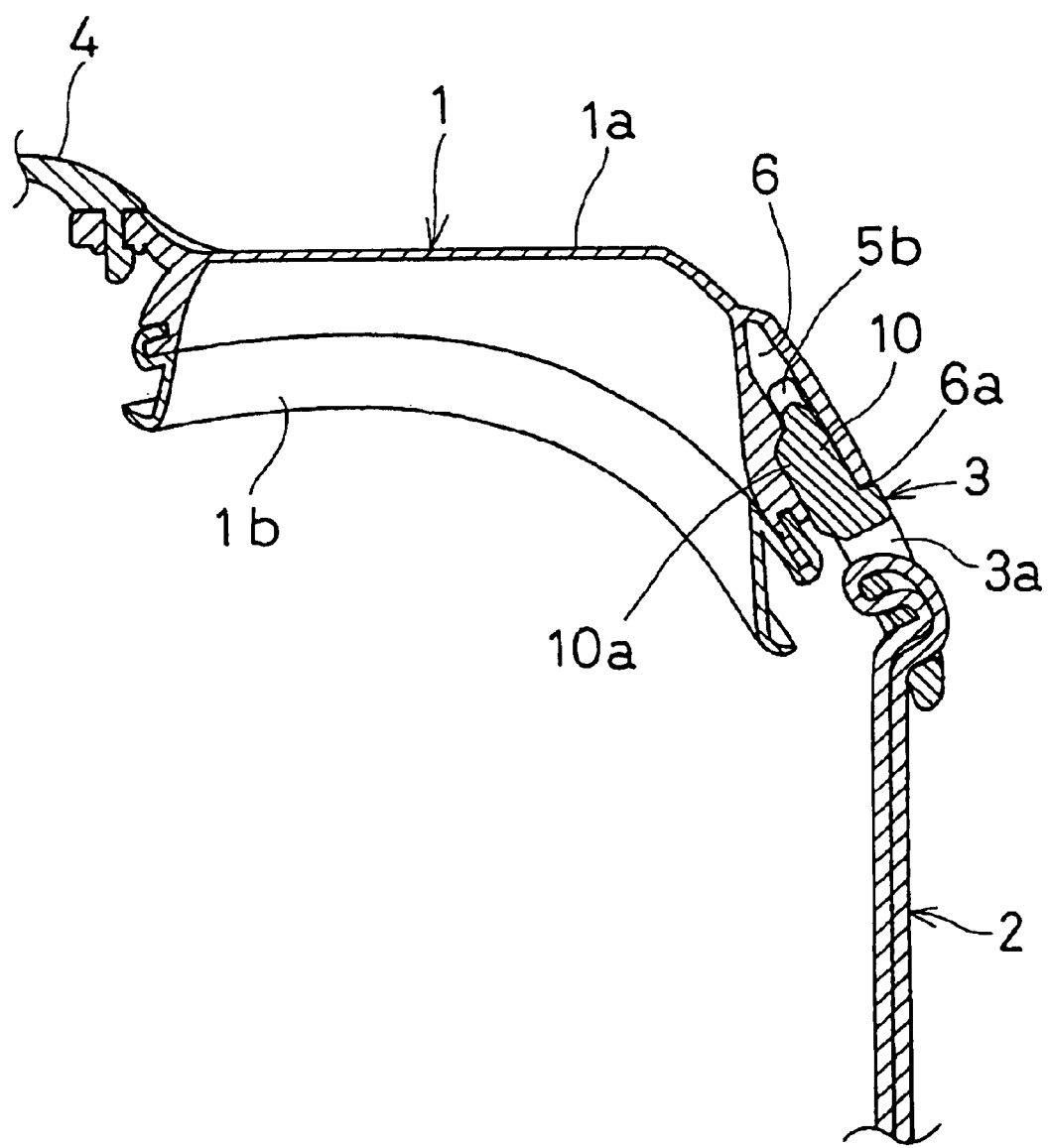
FIG. 3 is an enlarged sectional view of essential parts of the goggles according to the present invention.
Figure 4:
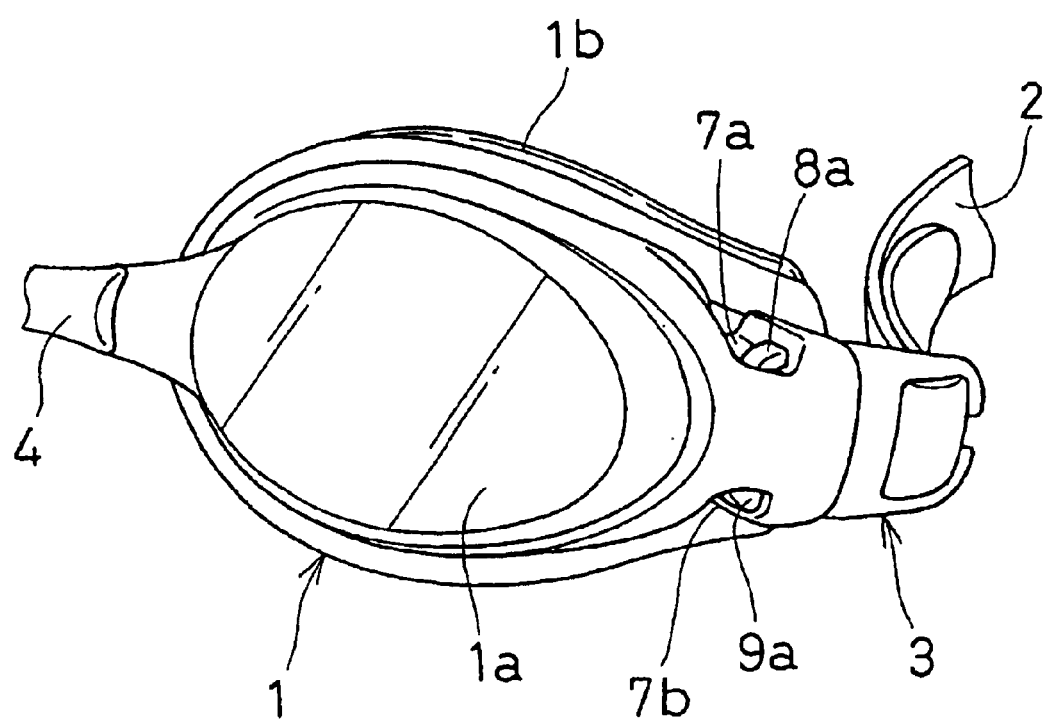
FIG. 4 is a perspective view showing a connected state between a goggle body and a connecting member of the goggles according to the present invention.

Goggles of the present invention, more specifically swimming goggles, are illustrated in FIGS. 1 to 8. The goggles include a goggle body 1, often referred to as an eye-cup and protecting eyes of a wearer, and a headband 2 to be put on the wearer's head. Both end portions of the headband 2 are connected with both end portions of the goggle body 1 through respective connecting members 3.

The goggle body 1 includes a lens portion 1a and a resilient face abutment portion 1b. In the drawings, they are formed separately but attached detachably. They may be formed in one unit body fixed by welding. In addition, in the drawings, the lens portion 1a of the goggle body 1 is formed with two right and left eye-cups (for a right eye and a left eye) bridged together with a resilient member 4. However, the lens portion 1a may be formed with one eye-cup.

Figure 5:
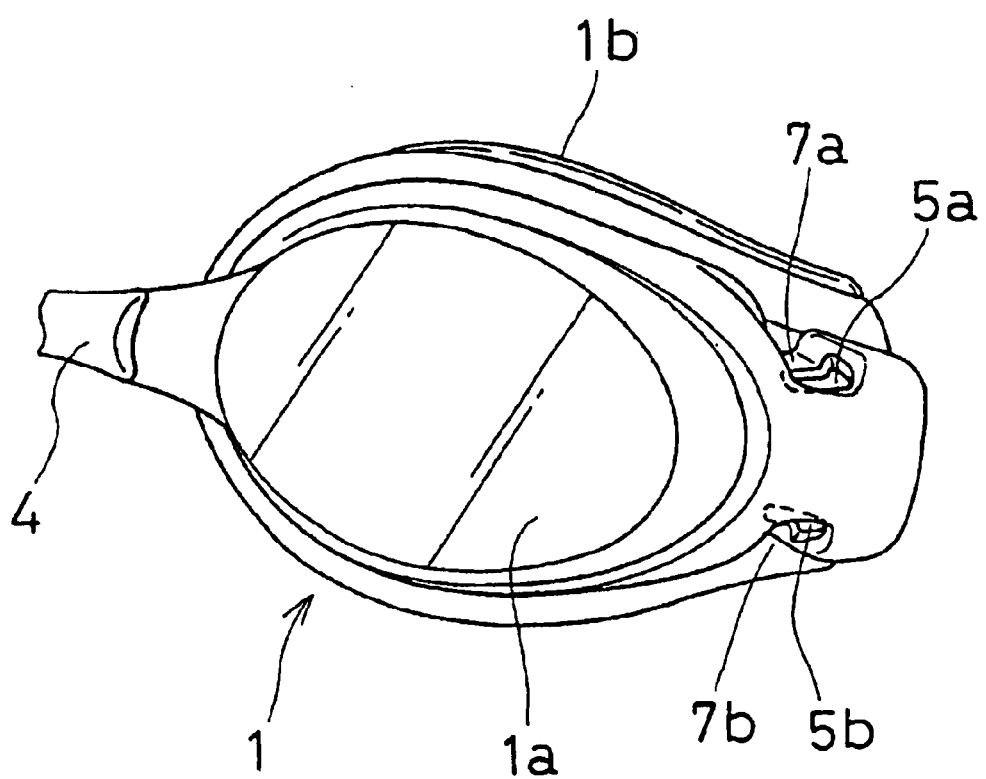
FIG. 5 is a partial perspective view of the goggle body of the goggles according to the present invention.
Figure 8:
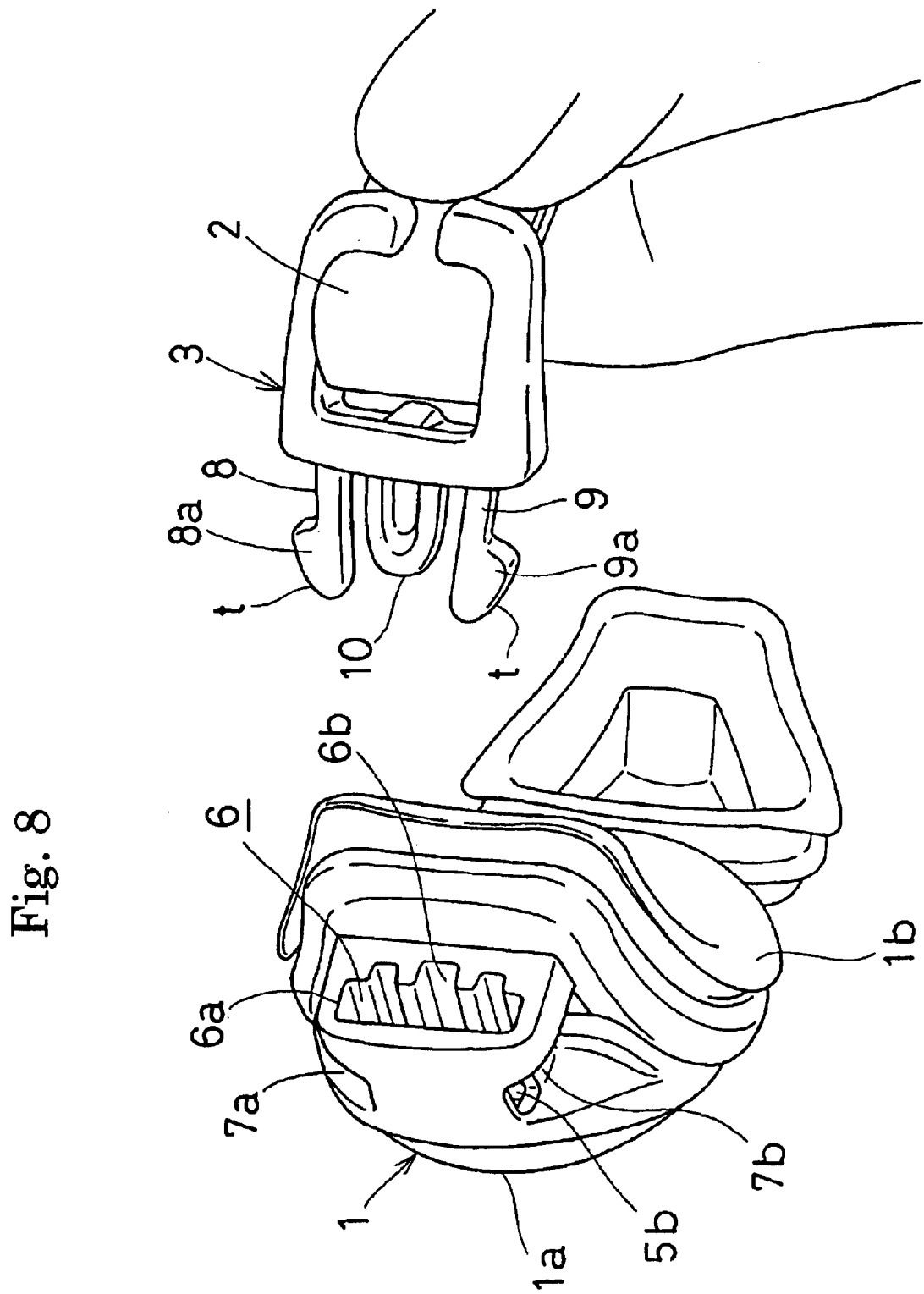
FIG. 8 is a perspective view showing a state in which the goggle body and the connecting member of the goggles according to the present invention are separated from each other.

As shown in FIGS. 5 and 8, each of end portions of the goggle body 1 has fitting apertures 5a and 5b open upward and downward, and an insertion (pushing-into and pulling-out) path 6 with single insertion port 6a which connects to the fitting apertures 5a and 5b and is open to a lateral end side. The insertion path 6 is provided with a guide groove 6b formed in an insertion and seperation direction of the connecting member 3. The fitting apertures 5a and 5b are provided on recessed portions 7a and 7b formed at both of the end portions of goggle body 1, as seen in the drawings.

The headband 2 is made of elastic material such as elastomer, and in general, formed in a band shape as a whole. However, as long as the end portions thereof have shapes attachable to the connecting members 3, the headband 2 does not necessarily have to be made in a band shape as a whole.

Figure 6:
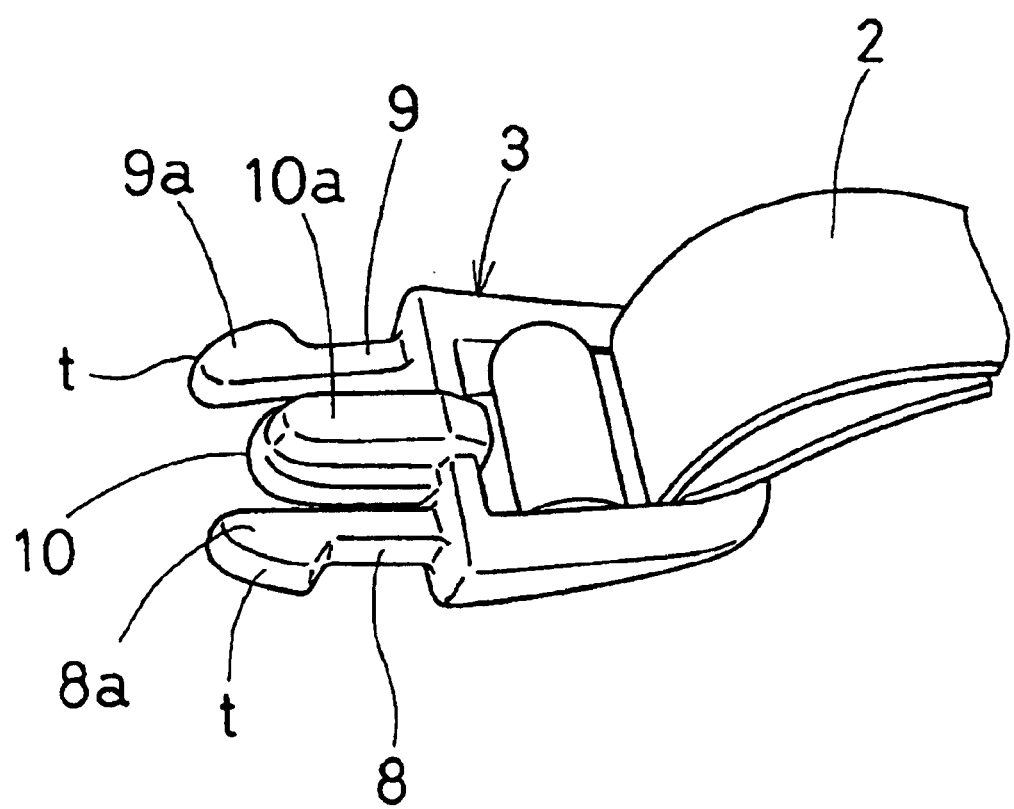
FIG. 6 is a perspective view of the connecting member of the goggles according to the present invention.

The connecting member 3 is illustrated in FIGS. 6 and 8. The connecting member 3 has, on its one end, an attaching hole 3a and the headband 2 is attached therethrough. The other end of the connecting member 3 has resilient insertion pieces 8 and 9 which respectively have protruded portions 8a and 9a. The protruded portions 8a and 9a are respectively fitted in the fitting apertures 5a and 5b and projects out from the goggles upwardly or downwardly. The protruded portions 8a and 9a of the resilient insertions piece 8 and 9 respectively have tapered portions t. Therefore, at the time of connecting the goggle body 1 and the connecting member 3, the resilient insertion pieces 8 and 9 are bent closer inwardly due to abutting against the port edge of the insertion port 6a of the insertion path 6 of the goggle body 1 and due to the existence of the tapered portions t, then the resilient insertion pieces 8 and 9 are naturally inserted into the insertion path 6 through the insertion port 6a. On the other hand, at the time of separating the connecting member 3 from the goggle body 1, a wearer may press the protruded portions 8 and 9 mutually down inwardly with his or her thumb and index finger, not only with his or her thumb, and pull the connecting member 3 out in the separation direction. This allows the wearer to easily and reliably manipulate the connecting member 3. Also the other end portion of the connecting member 3 is further provided with a guide piece 10 projecting in the insertion direction between and substantially parallel to the resilient insertion pieces 8 and 9. The guide piece 10 has a linearly raised rib 10a thereon. Still further, the guide piece 10 has a wider base portion and the linearly raised rib 10a is narrower than the base portion with both the base portion and the linearly raised rib 10a extending in the insertion and separation direction. The linearly raised rib is received in and guided along with the guide groove 6b of the insertion path 6 of the goggle body 1. The protruded portions 8a and 9a of the resilient insertion pieces 8 and 9 come into and become fitted in the fitting apertures 5a and 5b and then come out therefrom upwardly and downwardly, however, in case the fitting apertures 5a and 5b are formed in the recessed portions 7a and 7b of both of the end portions of the goggle body 1, the protruded portions 8a and 9a will not stick out largely from the contour of both end portions of the goggle body 1 and the goggles may keep its neat configuration.

In the goggles of the present invention as stated above, at the time of connecting the goggle body 1 and the connecting member 3, the resilient insertion pieces 8 and 9 of the connecting member 3 are pushed into the insertion path 6 through the insertion port 6a of the goggle body 1. Then the protruded portions 8a and 9a of the resilient insertion pieces 8 and 9 come to abut against the port edge of the insertion port 6a of the insertion path 6, and the resilient insertion pieces 8 and 9 inwardly bend and are smoothly inserted into the insertion path 6 through the insertion port 6a. In this case, the rib 10a of the guide piece 10 between the resilient insertion pieces 8 and 9 is received in and guided along with the guide groove 6b of the insertion path 6, and the resilient insertion pieces 8 and 9 are readily inserted into the insertion path 6. Subsequently, the protruded portions 8a and 9a of the resilient insertion pieces 8 and 9 come to fit in the fitting apertures 5a and 5b formed at the end portion of the goggle body 1, thereby the connected engagement between the goggle body 1 and the connecting member 3 is obtained and maintained.

Figure 7:
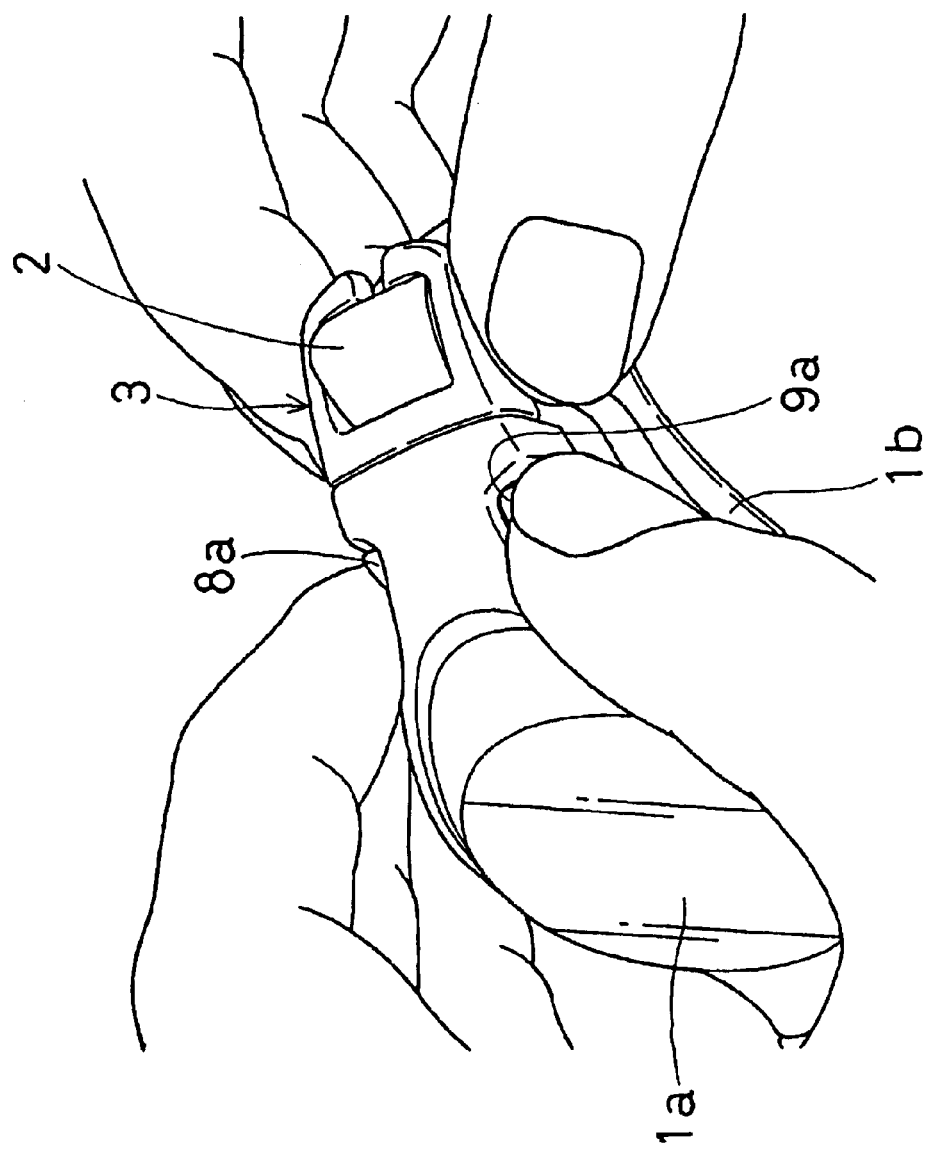
FIG. 7 is a perspective view showing a state in which the connecting member is about to be released from the goggle body of the goggles according to the present invention.

Furthermore, in the goggles of the present invention, at the time of releasing the connecting member 3 from the goggle body 1, as shown in FIG. 7, a wearer may hold and press the protruded portions 8a and 9a of the resilient insertion pieces 8 and 9 with his or her thumb and index finger and pull the connecting member 3 out in the separation direction. This leads to pulling the resilient insertion pieces 8 and 9 out from the insertion path 6, as shown in FIG. 8. In this case, again, the rib 10a of the guide piece 10 positioned between the resilient insertion pieces 8 and 9 is guided along with the guide groove 6b of the insertion path 6, so that the resilient insertion pieces 8 and 9 are smoothly pulled out from the insertion path 6.

In the goggles of the present invention structured stated above, at the time of separating the connecting member from the goggle body, a wearer can manipulate the connecting member with his or thumb and index finger, not only his or her thumb, and therefore easy and reliable manipulations become possible. And reliable connection between the goggle body and the connecting member is obtained. Furthermore, even if an outer force from front is applied on the goggles in use, the connected engagement between the goggle body and the connecting member is not inadvertently released.

What is claimed is:

1. Goggles having a goggle body and a headband which respectively have lateral end portions, associated end portions of the goggle body and the headband being connected together through respective connecting members, comprising:

at least one of the end portions of the goggle body being provided with an upper fitting aperture and a lower fitting aperture respectively open upwardly and downwardly, and an insertion path connecting to the apertures and being provided with a single insertion port open to the lateral end; and at least one of the connecting members being provided on a goggle body side with two resilient insertion pieces which are received through the single insertion port and have protruded portions which become to fit in the fitting apertures and come out upwardly and downwardly therefrom, tip portions of the protruded portions being tapered so as to be narrower toward the goggle body; and wherein the insertion path has a guide groove extending in an insertion and separation direction of the connecting member, the connecting member has a guide piece between and substantially parallel with the resilient insertion pieces, and the guide piece comprises a base portion and a rib provided thereon which extends in the insertion and separation direction of the connecting member, is received in and guided along with the guide groove, and the base portion is wider than the linearly raised rib.

2. The goggles according to claim 1, wherein the fitting apertures are provided in recessed portions formed on at least one of the end portions of the goggle body.

3. The goggles according to claim 2, wherein a distance between traversal outer edges of root parts of the resilient insertion pieces are substantially equal to a transverse width of the single aperture of the insertion path.

4. The goggles according to claim 1, wherein a length of the guide piece is shorter than that of the resilient insertion pieces.

5. The goggles according to claim 4, wherein a distance front outer edges of root parts of the resilient insertion piece are substantially equal to a transverse width of the single aperture of the insertion path.

6. The goggles according to claim 1, wherein a distance between traversal outer edges of root parts of the resilient insertion pieces are substantially equal to a transverse width of the single aperture of the insertion path.

* * * * *